(12) United States Patent
Malmin

(10) Patent No.: US 7,655,913 B2
(45) Date of Patent: Feb. 2, 2010

(54) CORRECTING MISALIGNMENT EFFECTS IN RECONSTRUCTED NUCLEAR MEDICAL IMAGES

(75) Inventor: Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 295 days.

(21) Appl. No.: 11/541,162

(22) Filed: Sep. 29, 2006

(65) Prior Publication Data

US 2007/0075250 A1 Apr. 5, 2007

Related U.S. Application Data

(60) Provisional application No. 60/722,508, filed on Sep. 30, 2005.

(51) Int. Cl.
*G01T 1/161* (2006.01)

(52) U.S. Cl. .................................. 250/363.03

(58) Field of Classification Search ............ 250/363.04, 250/363.08, 363.09, 252.1
See application file for complete search history.

(56) References Cited

U.S. PATENT DOCUMENTS

| | | | |
|---|---|---|---|
| 7,365,334 B1* | 4/2008 | Gordon | 250/363.04 |
| 2005/0165294 A1* | 7/2005 | Weiss | 600/410 |
| 2006/0214097 A1* | 9/2006 | Wang et al. | 250/252.1 |

* cited by examiner

*Primary Examiner*—David P Porta
*Assistant Examiner*—Djura Malevic
(74) *Attorney, Agent, or Firm*—Peter L. Kendall

(57) ABSTRACT

A method and system of correcting misalignment effects in reconstructed images of a nuclear medical imaging apparatus includes calculating misalignments of a detector to accommodate for deflections (e.g., gravity induced deflections) of a detector (e.g., a cantilevered detector mounted for rotation movement about a patient) from a fixed coordinate system used for image data acquisition.

29 Claims, 6 Drawing Sheets

θ GANTRY = 0

ROTATION ABOUT Zm
(YAW)

ROTATE ABOUT Ym
(ROLL)

ROTATION ABOUT Xm
(PITCH)

TRANSLATIONAL
SHIFT

CORRECTING MISALIGNMENT EFFECTS IN RECONSTRUCTED NUCLEAR MEDICAL IMAGES

CROSS-REFERENCE TO RELATED APPLICATIONS AND CLAIM FOR PRIORITY

This application claims priority under 35 U.S.C. §119(e) from provisional application Ser. No. 60/722,508 filed Sep. 30, 2005.

BACKGROUND OF THE INVENTION

1. Field of the Invention

The present invention relates to, inter alia, medical imaging systems, and, in particular, to techniques for correcting misalignment effects in reconstructed images, such as, e.g., for misaligned gamma cameras of nuclear medicine imaging systems and/or the like.

2. Background Discussion

1. General Background

A variety of medical imaging systems are known. Some illustrative imaging systems include nuclear medical imaging systems (e.g., gamma cameras), computed tomography (CT or CAT) systems, magnetic resonance imaging (MRI) systems, positron-emission tomography (PET) systems, ultrasound systems and/or the like.

With respect to nuclear medical imaging systems, nuclear medicine is a unique medical specialty wherein radiation (e.g., gamma radiation) is used to acquire images that show the function and/or anatomy of organs, bones and/or tissues of the body. Typically, radioactive compounds, called radiopharmaceuticals or tracers, are introduced into the body, either by injection or ingestion, and are attracted to specific organs, bones or tissues of interest. These radiopharmaceuticals produce gamma photon emissions that emanate from the body and are absorbed by a scintillation crystal, which produces flashes of light or "events." These events can be detected by an array of photo-detectors, such as photomultiplier tubes, and their spatial locations or positions can be calculated and stored. In this manner, an image of an organ, tissue or the like under study can be created from the detection of the distribution of the radioisotopes in the body. Typically, one or more detectors are used to detect the emitted gamma photons, and the information collected from the detector(s) is processed to calculate the position of origin of the emitted photon from the source (i.e., the body organ or tissue under study). The accumulation of a large number of emitted gamma positions allows an image of the organ or tissue under study to be displayed.

FIG. 1 depicts components of a typical nuclear medical imaging system 100 (i.e., having a gamma or scintillation camera) which includes a gantry 102 supporting one or more detectors 108 enclosed within a metal housing and movably supported proximate a patient 106 located on a patient support (e.g., pallet or table) 104. Typically, the positions of the detectors 108 can be changed to a variety of orientations to obtain images of a patient's body from various angles and locations along the patient's body. In many instances, a data acquisition console 200 (e.g., with a user interface and/or display) is located proximate a patient during use for a technologist 107 to manipulate during data acquisition. In addition to the data acquisition console 200, images are often "reconstructed" or developed from the acquired image data ("projection data") via a processing computer system which is operated at another image processing computer console including, e.g., an operator interface and a display, which may often be located in another room, to develop images. By way of example, the image acquisition data may, in some instances, be transmitted to the processing computer system after acquisition using the acquisition console.

Nuclear medicine imaging typically involves the assessment of a radionuclide distribution within a patient after the in vivo administration of radiopharmaceuticals. Imaging systems that assess radionuclide distribution include radiation detectors and acquisition electronics. Typically, the imaging systems detect x-ray or gamma ray photons derived from the administered radionuclides. Single photon emission imaging and coincidence imaging are two forms of nuclear medicine imaging that are currently in common use. In single photon emission imaging, the radionuclide itself directly emits the radiation to be assessed. For example, in Single Photon Emission Computed Tomography (SPECT), γ-emitting radionuclides such as $^{99m}$Tc, $^{123}$I, $^{67}$Ga and $^{111}$In may be part of the administered radiopharmaceutical.

Detectors used in such single photon emission imaging often use collimators placed between the patient and the gamma ray camera of the detector. In general, the collimators help to eliminate substantially all photons but those photons traveling in a desired direction from impinging on the detector surface. This is desirable to prevent scattered or background radiation photons from spuriously contributing to the image, and thereby causing inaccuracies. For example, a parallel hole collimator helps to eliminate from detection photons traveling in all directions except those almost perpendicular to the surface of the detector. The energy of emitted photons as well as their location of origin may then be accumulated until a satisfactory amount of projection data is acquired to allow the reconstruction of a clinically significant image.

Coincidence imaging helps to eliminate the need for such a collimator by relying on the detection of two oppositely traveling gamma photons, emitted as a result of the annihilation of a positron, at oppositely located detectors at nearly the same time. An example of coincidence imaging in current clinical use is Positron Emission Tomography (PET).

Typically, radiation detectors used in nuclear medicine imaging need to absorb x- or gamma-ray photons in an energy range typically between 1 keV and several MeV. These imaging photons are the photons either directly emitted or resulting from radionuclides within a patient. In order to stop spurious photons of similar energies with a collimator in SPECT imaging, a material with a high density and a high atomic number (Z) is necessary. Lead is the most common material used for collimators, but other materials such as, e.g., tungsten may also be used.

Typically, in radiology, detectors used clinically only integrate the energy deposited by a beam. However, a new generation of detectors for digital radiography and computed tomography (CT) can obtain extra information by counting individual photons and measuring their energy.

With respect to scintillators, a variety of scintillators are known. For example, scintillators include, e.g., continuous single slab, pixilated and/or columnar grow crystals. As for radionuclide imagers with pixilated radiation detector elements, typically cadmium zinc telluride ("CZT") crystals have recently been developed. In these pixilated radionuclide imagers, the intrinsic spatial resolution is defined by the size of the individual pixilated detector elements, rather than the separation between collimator holes. See, e.g., U.S. Pat. No. 6,838,672, assigned to the present assignee, the entire disclosure of which is incorporated herein by reference. With respect to the use of CZT as a solid state (i.e., semiconductor)

detector material, as a single photon detector, CZT is typically superior to NaI in several performance parameters. Among other things, the count rate capability for CZT detectors is virtually unlimited as compared to a typical scintillator crystal, because each pixel (or picture element) of the CZT material can act as an independent detector. Thus, unlike a typical scintillator crystal, in which two events occurring very close in time and spatial location will produce overlapping light output, two gamma photons arriving at exactly the same time in adjacent pixels of a CZT detector could be independently detected and measured accurately with respect to energy, given an optimum electronic circuitry design.

2. Gantry Misalignments

Current tomographic reconstructions rely on center-of-rotation (COR) and multi-head-registration (MHR) calibration schemes to correct for errors in the alignments of gantry/detector systems. These schemes are capable of removing the effects of certain misalignments (e.g., pure translational offsets and the average effects of angular misalignments). These "correctable" components are corrected by shifting the projection data before or during reconstruction and by correcting the angle at which the data are back projected.

Other components of resolution loss cannot be removed by simple manipulation of the projection data because the misalignment causes blurring in the axial dimension. That is, the image of a point source oscillates axially in the projection images and the oscillation depends on the location of the source within the object.

For gantries with cantilevered heads, this is a particular problem because of head droop. Head droop causes significant non-correctable axial blurring, which not only distorts sagital and coronal images, but reduces contrast in transaxial images (because the counts are misplaced into other slices). In addition, reducing head droop via more rigid mechanics is expensive.

While a variety of background technologies exist, there is a continued need in the art for improved systems and methods for, among other things, accommodating for misalignments in detectors.

SUMMARY OF THE PREFERRED EMBODIMENTS

The preferred embodiments of the present invention can significantly improve upon existing methods and/or apparatuses for, among other things, accommodating for misalignments in detectors.

According to some embodiments, a method of correcting detector misalignment effects in reconstructed images of a medical imaging apparatus with rotating detectors is performed that includes: calculating misalignments of a detector corresponding to yaw and pitch of the detector. In some examples, the calculating includes accounting for misalignments in a generally central normal position, $Z_e$, of the detector from being substantially orthogonal to the axis of rotation and in a generally horizontal axis, $Y_e$, of the detector from being substantially parallel to a substantially horizontal axis, $Y_m$, of movement of the imaged object. In some examples, the method further includes calculating misalignments of the detector corresponding to roll of the detector. In some examples, the method further includes calculating misalignments to accommodate for gravity-induced deflections of a detector. In some preferred examples, the method includes incorporating the misalignments into forward projection and/or back projection steps. In the preferred embodiments, the medical imaging system is a nuclear medical imaging system.

According to some other embodiments, a method of correcting detector/gantry misalignment effects in reconstructed images of an imaging apparatus in which detectors are moved relative to a patient is performed that includes: calculating misalignments of a detector using a 3-D iterative algorithm.

According to some other embodiments, a method of correcting detector/gantry misalignment effects in reconstructed images of an imaging apparatus having a cantilevered detector mounted for rotational movement about a patient is performed that includes: calculating misalignments of the cantilevered detector to accommodate for gravity-induced deflections of the detector. In some examples, the method further includes calculating misalignments of the detector corresponding to yaw, pitch and roll of the detector.

According to some embodiments, a nuclear medical imaging system is provided that includes: a) a detector mounted to move relative to a patient; b) the system being configured to improve resolution and contrast in tomographic images using a reconstruction algorithm that does not assume that a central normal is orthogonal to the axis of rotation of the detector and that the imaging y-axis is parallel to the axis of rotation.

The above and/or other embodiments, aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention, as well as further objects, features and advantages of the preferred embodiments will be more fully understood with reference to the following detailed description of the preferred embodiments, when taken in conjunction with the accompanying drawings, wherein.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Further to the above discussion regarding gantry misalignment and techniques to correct gantry misalignment in reconstructed images, according to some preferred embodiments, improved correction techniques are implemented which can fully remove all sources of resolution loss due to misalignment. In the preferred embodiments, the imaging system includes a computer or the like device that performs a 3-dimensional iterative reconstruction algorithm in which the forward-projection and back-projection steps incorporate all misalignments. In order to perform such calculations, the computer or the like device preferably has a high computational power. In this regard, with multi-processor, multi-gigahertz systems now available, such computer requirements can be reasonably achieved.

According to some embodiments, a system can be provided to address pointing errors in collimators. In such other embodiments, the detector/collimator surface can be, e.g., represented by an image of direction vectors (e.g., normal for a perfect parallel beam system). Preferably, the direction vectors can then be adjusted to account for misalignments and a pixel-driven back projector used in reconstruction.

Illustrative Embodiments

The preferred embodiments provide a technique to improve resolution and contrast in tomographic images. In the most preferred embodiments, aspects described herein can be employed related to tomography in systems with rotating detectors, such as, e.g., SPECT cameras. However, in various other embodiments, aspects described herein can be implemented in other systems which do not have such rotating detectors. Embodiments of the present invention are not limited to systems with rotating detectors, but can be employed within any system within which misalignment of detectors can occur.

Figure 1:
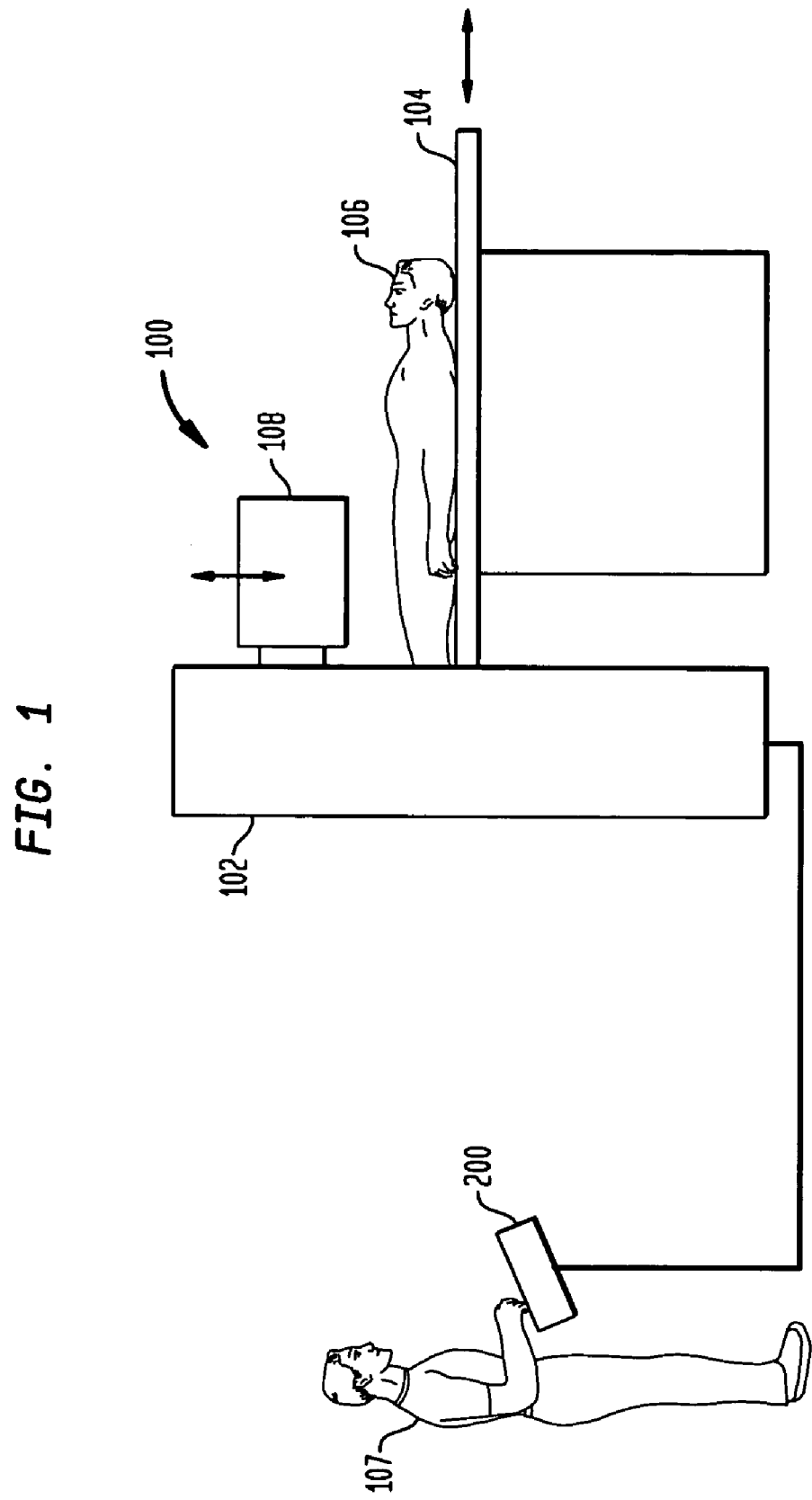
FIG. 1 is a side view of an illustrative nuclear medical imaging system or the like within which elements of the present invention may be employed in some illustrative and non-limiting embodiments.
Figure 2:
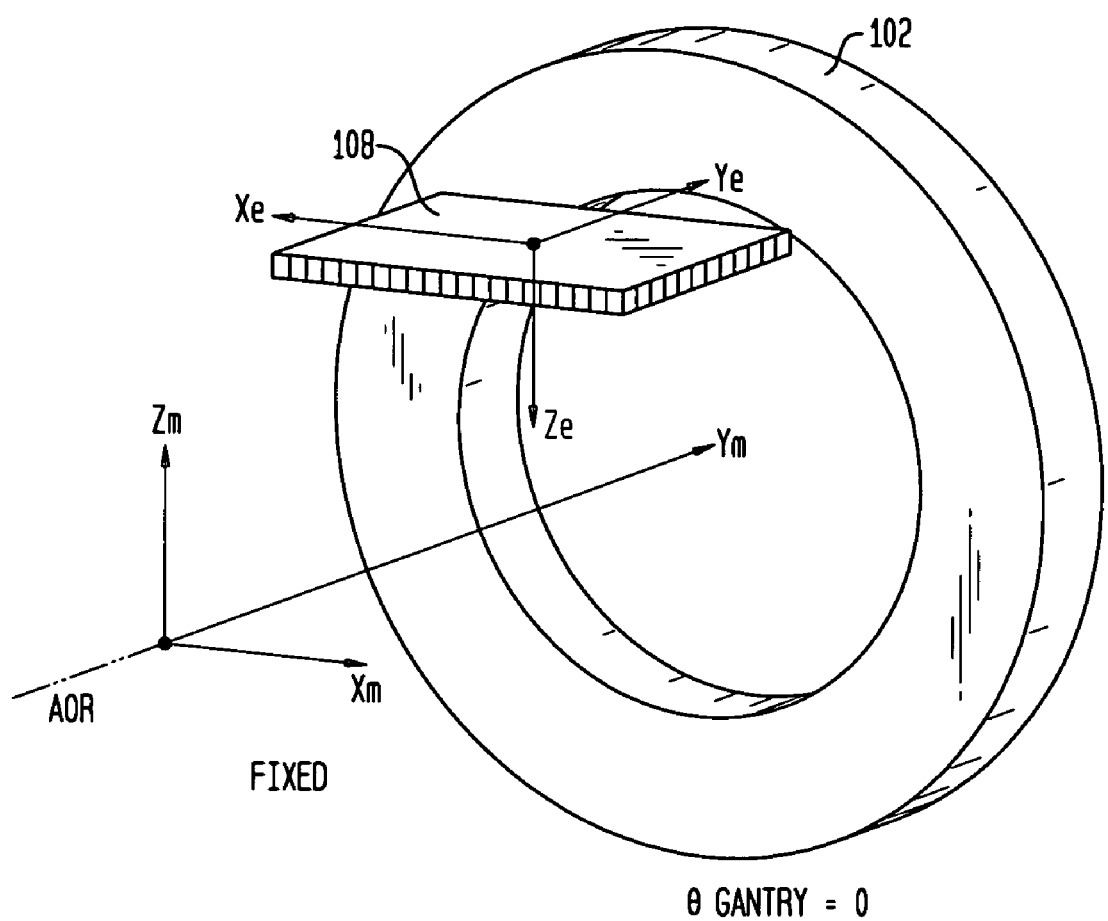
FIG. 2 is a diagram showing mechanical (e.g., gantry) and detector coordinate systems according to some illustrative embodiments.

FIG. 2 shows an illustrative detector 108 (such as, e.g., a nuclear medical imaging detector) mounted in a manner so as to rotate upon a gantry 102, similar to that shown in FIG. 1. FIG. 2 is a reference diagram that shows mechanical (e.g., gantry) and detector coordinate systems. As depicted in this example, the detector 108 rotates about a mechanical axis of rotation (AOR), $Y_m$. An object to be imaged, such as, e.g., a patient, is placed on the axis of rotation and 2-D projection images, $[X_e, Y_e]$, are acquired at a sequence of gantry angles, θ. In some preferred embodiments, a collimator limits the projection view direction substantially to that of the central normal to the detector surface, $Z_e$. Typically, the center of projection image is assumed to coincide with $Z_e$.

As discussed above, existing reconstruction algorithms implicitly assume that the central normal, $Z_e$, is orthogonal to the axis of rotation and that the imaging y-axis, $Y_e$, is parallel to $Y_m$. With these assumptions, reconstruction of a full 3-D volume has been performed using individual 2-D projection data from each of a large number of gantry or projection angles θ. These assumptions, however, are not strictly true. Among other things, mechanical tolerances can produce misalignments of gantry components. In addition, gravity can produce mechanical deflections and these deflections can change with the rotation angle or position of the detector. Previously, the effects of these misalignments on the reconstructed resolution had been masked by the dominant effect of collimator resolution, with reconstructed resolution approximately equal to the attenuation-weighted average of collimator resolution in the projections. In this regime, only "zero-order" corrections for detector misalignments had been utilized (i.e., as described above MHR and COR).

However, with the rising prominence of molecular imaging and the advent of, e.g., FLASH 3D reconstruction (resolution recovery), higher resolution systems having more detailed corrections are desirable. Iterative reconstruction algorithms (such as, e.g., FLASH 3D) are capable of resolution recovery because they can include the physics of the acquisition process within the reconstruction algorithm—e.g., attenuation, scatter, and especially collimator resolution. In the preferred embodiments, a full set of gantry misalignments are added into the model of the acquisition process.

FIGS. 3(A) to 3(D) depict schematically the basic misalignments experienced by a detector/gantry system. In this disclosure, certain misalignments are referenced in terms of "yaw, pitch, roll" of the detector. In this disclosure, these are identified as φ for "yaw," γ for "pitch," and η for "roll" in a manner similar to, e.g., use of the terminology in aviation.

Figure 3A:
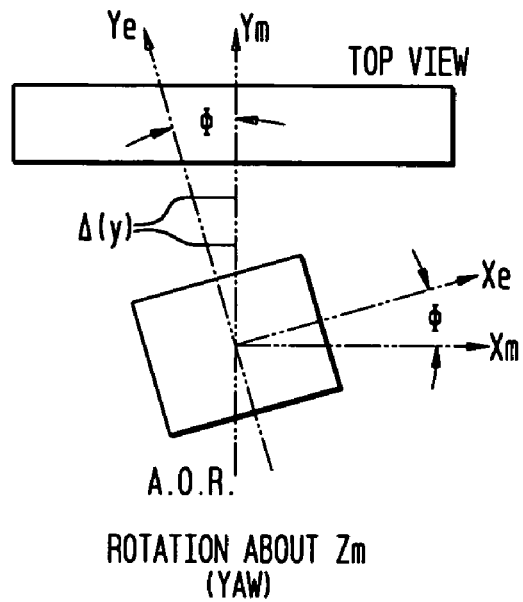
FIGS. 3(A) to 3(D) are diagrams that schematically depict basic misalignments of a detector/gantry system according to some embodiments.
Figure 3B:
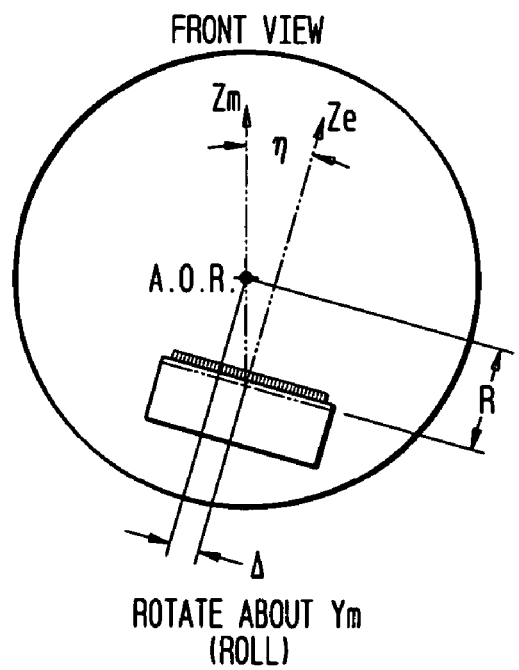
Figure 3C:
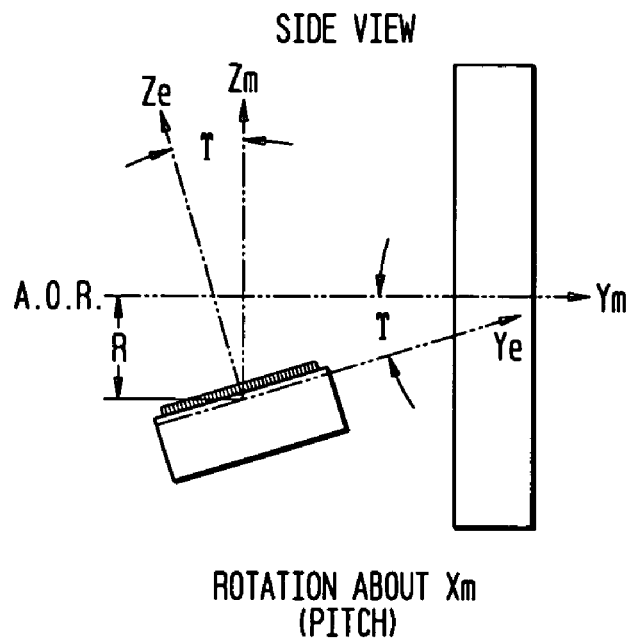

In particular, FIG. 3(A) illustrates how illustrative yaw misalignments can occur about the axis $Z_m$ (e.g., discrepancies between $Y_e$-$Y_m$ axes and $X_e$-$X_m$ axes); FIG. 3(B) illustrates how illustrative roll misalignments can occur about the axis $Y_m$ (e.g., discrepancies between $Z_m$ and $Z_e$ axes); FIG. 3(C) illustrates how illustrative pitch misalignments can occur about the axis $X_m$ (e.g., discrepancies between $Y_e$-$Y_m$ axes and $Z_e$-$Z_m$ axes) according to some illustrative and non-limiting examples.

In FIGS. 3(A) to 3(D), the following reference numerals are depicted.

R=Which represents the radius of rotation (ROR), or the distance from the detector interaction plane to the axis of rotation (AOR).

AOR=Which represents the mechanical axis of rotation (AOR), $Y_m$. As shown in FIG. 2, this points in the direction of the gantry from the detector.

Figure 3D:
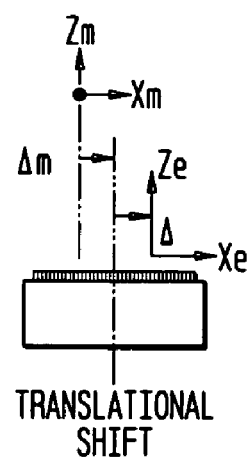

$\Delta X_{mech}$=Which represents the mechanical shift of the physical center of the collimator/crystal relative to the axis of rotation (AOR), $Y_m$, as shown in FIG. 3(D).

$\Delta X_{electronic}$=Which represents, by way of example, a shift of an imaging grid relative to the center of the collimator/crystal.

φ (Yaw)=Which represents the angular misalignment due to rotation of the detector about the $Z_m$ axis (such as, e.g., due to the rotation of the detector within a tub, tub within a yoke, or the like).

γ (Pitch)=Which represents the angular misalignment due to rotation of the detector about the $X_m$ axis (such as, e.g., erroneous caudal tilt).

η (Roll)=Which represents the angular misalignment due to rotation of the detector about the $Y_m$ axis.

r=Which represents the distance of a point source object from the AOR (e.g., $=(x^2+z^2)^{1/2}$).

In the preferred embodiments, the system is configured so as to account for at least some, preferably all, of the following misalignments in the reconstruction of the images:

1. $COR_x$=which involves, e.g., a translational shift of center of projection relative to the axis of rotation (AOR), and which has the following two parts:
   a. $\Delta X_{mech}$=which, as shown in FIG. 3(D) involves, e.g., a mechanical shift of physical center of detector (e.g., collimator/crystal) relative to the axis of rotation (AOR), $Y_m$.
   b. $\Delta X_{electronic}$=which involves, e.g., a shift of an imaging grid relative to center of, e.g., a collimator/crystal. It is noted that for non-focusing collimators $\Delta x_{mech}$ and $\Delta x_{electronic}$ are effectively indistinguishable.
2. $\Delta Y_{head}$=which involves, e.g., a Y-shift of heads relative to an average common value.

3. Angular accuracy/roll (see, e.g., η shown in FIG. 3(B)), which involves, e.g., an angular misalignment due to misalignment/rotation of detector about the $Y_m$ axis.
4. "Yaw" error (see, e.g., (ρ shown in FIG. 3(A)), which involves, e.g., an angular misalignment due to rotation of detector about the $Z_m$ axis (e.g., rotation of detector within tub or tub within yoke).
5. "Pitch" error (see, e.g., γ FIG. 3(C)), which involves, e.g., an angular misalignment due to rotation of detector about the $X_m$ axis. This degree of freedom is often referred to as caudal tilt.

Existing systems do not fully address these misalignments, but merely address limited discrepancies:

For example, some corrections for misalignments at numbers 1-3 above are addressed with MHR or multi-head registration correction.

As another example, misalignment at number 4—i.e., roll—is only partially addressed (for the single detector calibration radius) by the $COR_x$ correction (assuming a constant η).

As another example, misalignment at number 5 above is only partially addressed by the Y-dependence of the $COR_x$ correction (assuming a constant φ).

In general, pure translational errors can be completely corrected with essentially no loss of resolution. Angular errors can only be partially corrected in 2-D reconstruction, but leave a residual blur.

In contrast to prior systems and methods, the preferred embodiments can account for, e.g., detector misalignments using algorithms that do not assume that a central normal is orthogonal to the axis of rotation of the detector and that the imaging y-axis is parallel to said axis of rotation.

In some illustrative and non-limiting embodiments, the following equations (1a) and (1b) can be used to define the projection image coordinates [x', y'] of point object at [x, y, z] in the space-fixed system in terms of the fixed misalignments (independent of gantry angle):

$$x'=(\eta \cdot z-x)\cdot\cos(\theta)+(\eta \cdot x+z)\cdot\sin(\theta)[-\Delta_{mech}-\Delta_{electronic}]+ [-\eta \cdot R]+[\phi \cdot y] \quad \text{Eq. (1a)}$$

$$y'=(\phi \cdot x - y \cdot z)\cdot\cos(\theta)-(\gamma \cdot x+\phi \cdot z)\cdot\sin(\theta)+[y]+[\gamma \cdot R] \quad \text{Eq. (1b)}$$

Wherein:

$r=(x^2+z^2)^{1/2}$ is the distance of a point source object from the AOR.

Current 2-D reconstruction algorithms (and, e.g., FLASH 3D) essentially assume φ, γ, and η each equal 0. However, a [-η·R] term is essentially captured by the COR process. In addition, an MHR algorithm of SIEMENS MEDICAL SOLUTIONS also captures a [φ·y] term via the slice-dependent COR.

Figure 4:
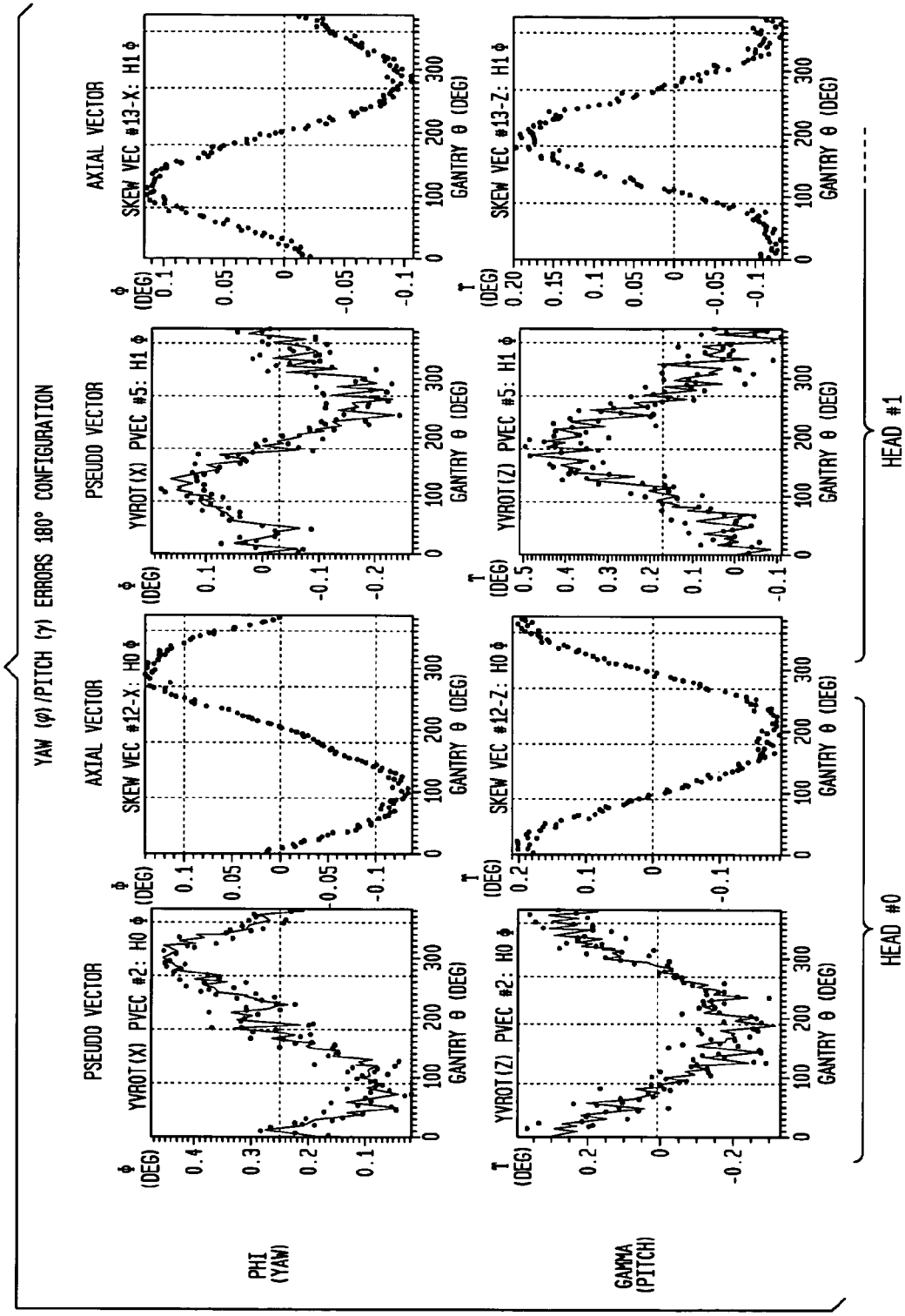
FIG. 4 is a diagram depicting yaw and pitch measurements for an illustrative 180 degree detector configuration.

In reality, φ, γ, η are not equal to zero and, indeed, vary with gantry angle due to, e.g., gravity-induced deflections. For illustrative purposes, FIG. 4 shows a plot of φ and γ measured for both heads on a SIEMENS nuclear medical imaging system model SYMBIA using a precision optical system (such as, e.g., OPTOTRAK of NORTHERN DIGITAL, INC.). In particular, FIG. 4 shows "yaw" and "pitch" measurements for a 180° configuration detector and gantry system.

In the illustrative examples, the yaw and pitch are measured by two techniques: "pseudo vectors" which include both fixed and angle-varying components; and "axial vectors" which measure only the angle dependent components (but at better accuracy). In these illustrative examples, both yaw and pitch show peak-to-peak~sinusoidal variations of about 0.3 to 0.5 degrees, large enough to cause visible degradation in a high resolution SPECT system. Notably, variations in roll (which are not shown) are smaller.

The deviations from a "perfect" gantry described above are not necessarily complete. Other deviations can be important for specific gantries—such as, by way of example only, $\Delta Y_{head}$ may vary with angle. In some embodiments, equations (1a) and (1b) can be modified to contain other terms describing deviations important for specific gantries.

In various embodiments, a variety of techniques for determining misalignments can be employed, including optical techniques, but in some embodiments, techniques other than optical misalignments can also be used to determine the parameters describing the deviation from a "perfect" or "appropriately positioned" detector/gantry. For instance, a constellation of ~5 point sources, placed to sample the full field of view, could be imaged over a 360° gantry rotation, and their [x', y'] locations in the projection data utilized to deduce the system misalignments via equations (1a) and (1b) using standard least squares fitting techniques.

In the preferred embodiments, parameters describing deviations from a perfect or properly aligned detector/gantry are obtained and used in the preferred embodiments of the invention. The determined parameters are then preferably employed within a fully 3-D iterative algorithm where the gantry-angle-dependent misalignments are explicitly incorporated into the forward projection and/or back projection steps (e.g., forward and back projection of data for use as correction data). See, e.g., for illustrative background on forward projection of data: (1) A. C. Kak and Malcolm Slaney, *Principles of Computerized Tomographic Imaging*, Society of Industrial and Applied Mathematics, 2001; (2) K. J. Lee and D. C. Barber, *Use Of Forward Projection To Correct Patient Motion During SPECT Imaging*, Phys. Med. Biol., 43 171-187 (1998). In the preferred embodiments, not only can resolution be improved, but money can be saved by enabling gantries and the like to be made in a less costly manner—e.g., allowing gantries which are not held to such tight mechanical tolerances.

Figure 5:
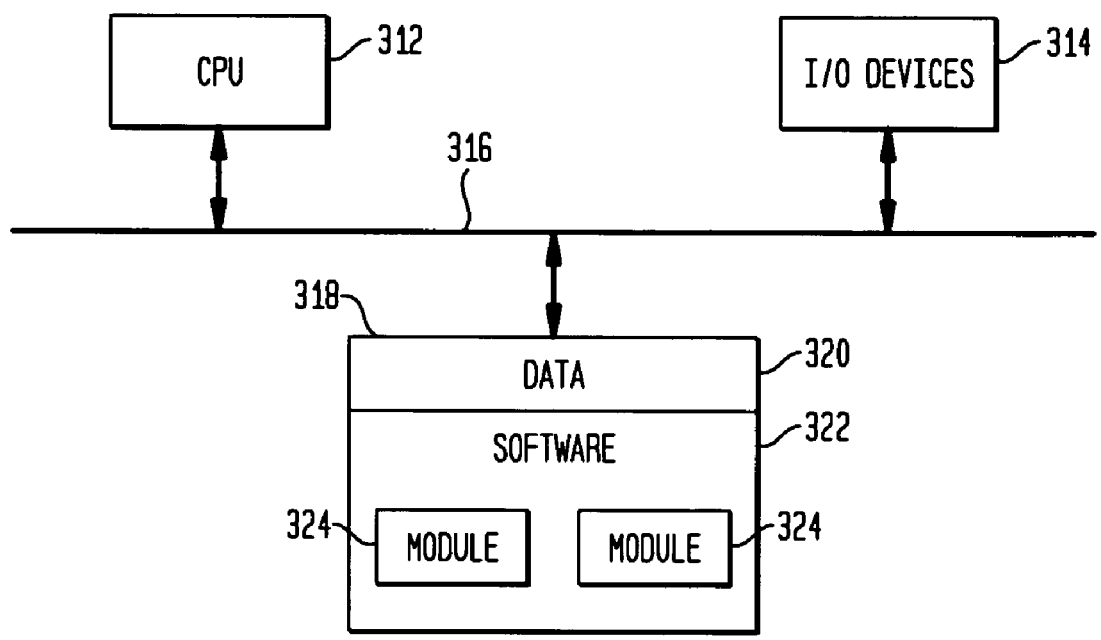
FIG. 5 is a schematic block diagram showing illustrative computer components that can be employed in some illustrative and non-limiting examples.

FIG. 5 shows components of an illustrative computer that can be used to implement computerized process steps to carry out some aspects of various embodiments of the invention. In some embodiments, the computer includes a central processing unit (CPU) 312, which can communicate with a set of input/output (I/O) device(s) 314 over a bus 316. The I/O devices 314 can include, for example, a keyboard, a mouse, a video monitor, a printer, and/or other devices. In some embodiments, the CPU 312 can communicate with a computer readable medium (e.g., conventional volatile or non-volatile data storage devices) 318 (hereafter "memory 318") over the bus 316. The interaction between a CPU 312, I/O devices 314, a bus 316, and a memory 318 can be like that known in the art. Memory 318 can include, e.g., data 320 and software 322. The software 322 can include a number of modules 324 (two modules are depicted for illustrative purposes only) for implementing the steps of processes. Conventional programming techniques may be used to implement these modules.

In some embodiments, the various methods described herein may be implemented via one or more computer program products for use with a computer system. This implementation may, for example, include a series of computer instructions fixed on a computer readable medium (e.g., a diskette, a CD-ROM, ROM or the like) or transmittable to a computer system via an interface device, such as a modem or the like. The transmission medium may be substantially tangible (e.g., communication lines) and/or substantially intangible (e.g., wireless media using microwave, light, infrared, etc.). The computer instructions can be written in various programming languages and/or can be stored in memory device(s), such as semiconductor devices (e.g., chips or circuits), magnetic devices, optical devices and/or other memory devices. In the various embodiments, the transmission may use any appropriate communications technology.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (for example, various aspects in different embodiments can be combined together when appropriate in various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

The invention claimed is:

1. A method performed by a processor of correcting detector misalignment effects in reconstructed images of an object from image data acquired by a medical imaging apparatus with rotating detectors, comprising:
calculating via the processor misalignments of a detector corresponding to at least yaw and pitch of the detector with respect to a fixed coordinate system; and
correcting said acquired image data based on said calculated misalignments;
wherein the step of calculating comprises defining projection image coordinates [x', y'] of a point object at [x, y, z] in said fixed coordinate system in terms of fixed misalignments.

2. The method of claim 1, wherein the step of calculating via the processor comprises accounting for misalignments in a generally central normal position, $Z_e$, of the detector from being substantially orthogonal to an axis of rotation and in a generally horizontal axis, $Y_e$, of the detector from being substantially parallel to a substantially horizontal axis, $Y_m$, of movement of the imaged object.

3. The method of claim 1, further comprising:
calculating via the processor misalignments of said detector corresponding to roll of the detector with respect to said fixed coordinate system.

4. The method of claim 1, further comprising:
calculating via the processor misalignments respectively related to a specific gantry of the medical imaging apparatus.

5. The method of claim 1, further including:
calculating via the processor misalignments related to gravity-induced deflections of a detector.

6. The method of claim 1, further comprising:
calculating via the processor misalignments related to gravity-induced deflections of a cantilevered detector.

7. The method of claim 1, further comprising:
calculating via the processor misalignments related to gravity-induced deflections of a cantilevered detector that rotates around an object during data acquisition.

8. The method of claim 1, further comprising:
incorporating calculated misalignments into forward projection and/or back projection image reconstruction steps.

9. The method of claim 1, wherein the step of calculating via the processor comprises applying at least one equation that defines the projection image coordinates independent of gantry angle.

10. The method of claim 9, further wherein:
the step of calculating via the processor misalignments is based on the following equations:

$$x' = (\eta \cdot z - x) \cdot \cos(\theta) + (\eta \cdot x + z) \cdot \sin(\theta)[-\Delta_{mech} - \Delta_{electronic}] + [-\eta \cdot R] + [\phi \cdot y], \text{ and}$$

$$y' = (\phi \cdot x - y \cdot z) \cdot \cos(\theta) - (y \cdot x + \phi \cdot z) \cdot \sin(\theta) + [y] + [y \cdot R],$$

wherein distance of a point source object from an axis of rotation is based on the following equation:

$$r = (x^2 + z^2)^{1/2}.$$

11. The method of claim 10, wherein said medical imaging apparatus comprises a nuclear medical imaging system.

12. A method performed by a processor of correcting detector/gantry misalignment effects in reconstructed images of an object from image data acquired by an imaging apparatus in which detectors are moved relative to said object, the method comprising:
calculating via the processor misalignments of a detector with respect to a fixed coordinate system using a 3-D iterative algorithm; and
correcting said acquired image data based on said calculated misalignments,
wherein the step of calculating comprises defining projection image coordinates [x', y'] of a point object at [x, y, z] in said fixed coordinate system in terms of fixed misalignments.

13. The method of claim 12, wherein said 3-D iterative algorithm accounts for misalignments in a generally central normal position, $Z_e$, of the detector from being substantially orthogonal to the axis of rotation and in a generally horizontal axis, $Y_e$, of the detector from being substantially parallel to a substantially horizontal axis, $Y_m$, of movement of the imaged object.

14. A method performed by a processor of correcting detector/gantry misalignment effects in reconstructed images of an object from image data acquired by an imaging apparatus having a cantilevered detector mounted for rotational movement about said object, the method comprising:
calculating via the processor misalignments of the cantilevered detector with respect to a fixed coordinate system to accommodate for gravity-induced deflections of the detector,
wherein the step of calculating comprises defining projection image coordinates [x', y'] of a point object at [x, y, z] in said fixed coordinate system in terms of fixed misalignments.

15. The method of claim 14, wherein the step of calculating via the processor further comprises accounting for misalignments in a generally central normal position, $Z_e$, of the detector from being substantially orthogonal to the axis of rotation and in a generally horizontal axis, $Y_e$, of the detector from being substantially parallel to a substantially horizontal axis, $Y_m$, of movement of the imaged object.

16. The method of claim 14, further comprises:
calculating via the processor misalignments of said imaging apparatus corresponding to yaw of the detector.

17. The method of claim 14, further comprises:
calculating via the processor misalignments of said imaging apparatus corresponding to pitch of the detector.

18. The method of claim 14, further comprises:
calculating via the processor misalignments of said imaging apparatus corresponding to roll of the detector.

19. The method of claim 14, further comprises:
calculating via the processor misalignments of said imaging apparatus corresponding to yaw, pitch and roll of the detector.

20. The method of claim 14, further comprises:
calculating via the processor misalignments of said imaging apparatus corresponding to angle dependent axial and transverse translations of the detector.

21. The method of claim 14, further comprises:
calculating via the processor misalignments to accommodate for gravity-induced deflections of a cantilevered detector that rotates around an object during data acquisition.

22. The method of claim 14, wherein said imaging apparatus comprises a nuclear medical imaging detector.

23. A nuclear medical imaging system, comprising:
a detector mounted to rotate relative to a patient placed along a fixed axis of rotation; and
a processor including an image reconstruction algorithm that accounts for a central normal offset from being orthogonal to the axis of rotation of the detector and for an imaging y-axis offset from being parallel to said axis of rotation,
wherein accounting for said offsets is based on at least one equation that defines projected image coordinates [x', y'] of a point object at [x, y, z] in a fixed coordinate system in terms of one or more fixed misalignments.

24. The system of claim 23, wherein said image reconstruction algorithm is embodied in software executing on said processor, and wherein said software calculates misalignments of said detector corresponding to yaw and pitch of the said detector with respect to said fixed coordinate system including said fixed axis of rotation.

25. The system of claim 24, wherein said software further calculates misalignments of said detector corresponding to roll of the detector with respect to said fixed coordinate system.

26. The system of claim 24, wherein said software accounts for misalignments in a generally central normal position, $Z_e$ of the detector from being substantially orthogonal to said axis of rotation and in a generally horizontal axis, $Y_e$, of the detector from being substantially parallel to a substantially horizontal axis, $Y_m$, of movement of the imaged patient.

27. The system of claim 24, wherein said software calculates misalignments to accommodate for gravity-induced deflections of a cantilevered detector that rotates around an object during data acquisition.

28. The system of claim 24, wherein said at least one equation further defines the projection image coordinates independent of gantry angle.

29. The system of claim 28, wherein said software calculates misalignments based on the following equations:

$$x'=(\eta \cdot z-x)\cdot\cos(\theta)+(\eta \cdot x+z)\cdot\sin(\theta)[-\Delta_{mech}-\Delta_{electronic}]+ [-\eta \cdot R]+[\phi \cdot y]; \text{ and}$$

$$y'=(\phi \cdot x-y\cdot z)\cdot\cos(\theta)-(y\cdot x+\phi \cdot z)\cdot\sin(\theta)+[y]+[y\cdot R],$$

wherein a distance of a point source object from the axis of rotation is based on the following equation:

$$r=(x^2+z^2)^{1/2}.$$

* * * * *